United States Patent
Elizondo et al.

(10) Patent No.: US 6,174,719 B1
(45) Date of Patent: *Jan. 16, 2001

(54) CARDIOVASCULAR BIOREACTOR APPARATUS AND METHOD

(75) Inventors: David R. Elizondo, St. Paul, MN (US); Todd D. Campbell, Hillsboro, OR (US); Robert P. Totten, Placerville, CA (US)

(73) Assignee: St. Jude Medical, Inc., St. Paul, MN (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/339,160

(22) Filed: Jun. 24, 1999

Related U.S. Application Data

(63) Continuation of application No. 08/796,573, filed on Feb. 6, 1997, now Pat. No. 5,916,800, which is a continuation of application No. 08/482,990, filed on Jun. 7, 1995, now abandoned.

(51) Int. Cl.⁷ .................................................. A01N 1/00
(52) U.S. Cl. .................................. 435/284.1; 435/286.5; 435/293.1; 600/36
(58) Field of Search ......................... 73/168, 866.4, 73/865.9, 37; 435/284.1, 286.5, 286.6, 293.1, 395, 402; 600/36; 633/1, 2

(56) References Cited

U.S. PATENT DOCUMENTS

| | | | |
|---|---|---|---|
| 3,639,084 | 2/1972 | Goldhaber | 435/284 |
| 3,753,865 | 8/1973 | Belzer et al. | 435/284 |
| 3,772,153 | 11/1973 | De Roissart | 435/284 |
| 3,777,507 | 12/1973 | Burton et al. | 435/284 |
| 3,843,455 | 10/1974 | Bier | 435/284 |
| 4,682,491 | * 7/1987 | Pickard | 73/37 |
| 4,745,759 | 5/1988 | Bauer et al. | 435/284 |
| 5,272,909 | * 12/1993 | Nguyen et al. | 73/37 |
| 5,285,657 | 2/1994 | Bacchi et al. | 435/284 |
| 5,326,706 | 7/1994 | Yland et al. | 435/284 |
| 5,338,662 | 8/1994 | Sadri | 435/284 |
| 5,362,622 | 11/1994 | O'Dell et al. | 435/284 |
| 5,792,603 | * 8/1998 | Dunkelman et al. | 435/1.2 |
| 5,846,828 | * 12/1998 | Peterson et al. | 435/399 |

* cited by examiner

Primary Examiner—David A. Redding
(74) Attorney, Agent, or Firm—Westman, Champlin & Kelly; Peter S. Dardi

(57) ABSTRACT

The invention involves a method and apparatus for processing biological material, such as heart valves and vascular grafts.

20 Claims, 6 Drawing Sheets

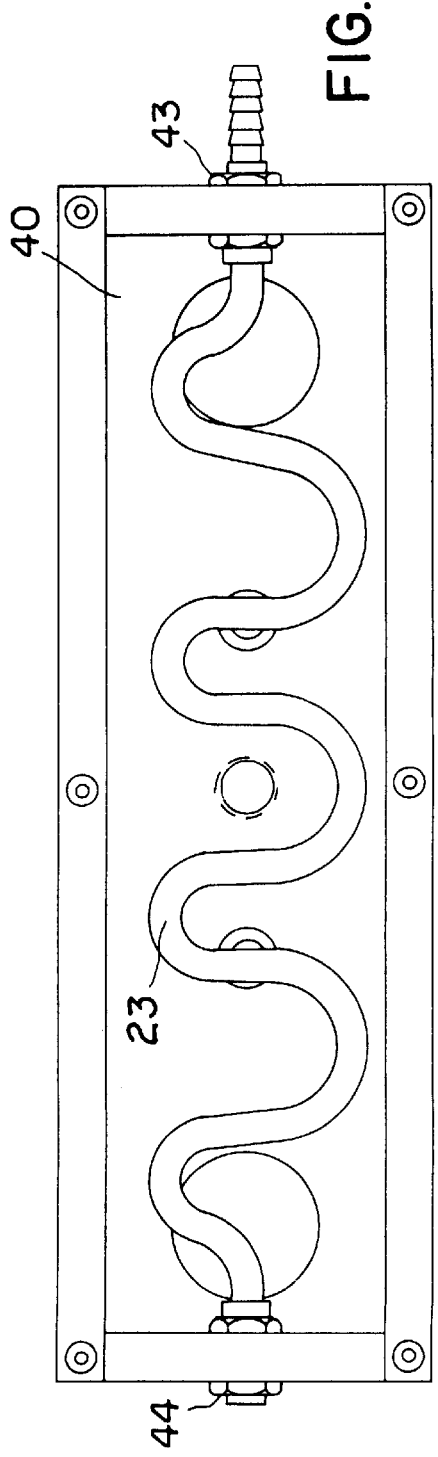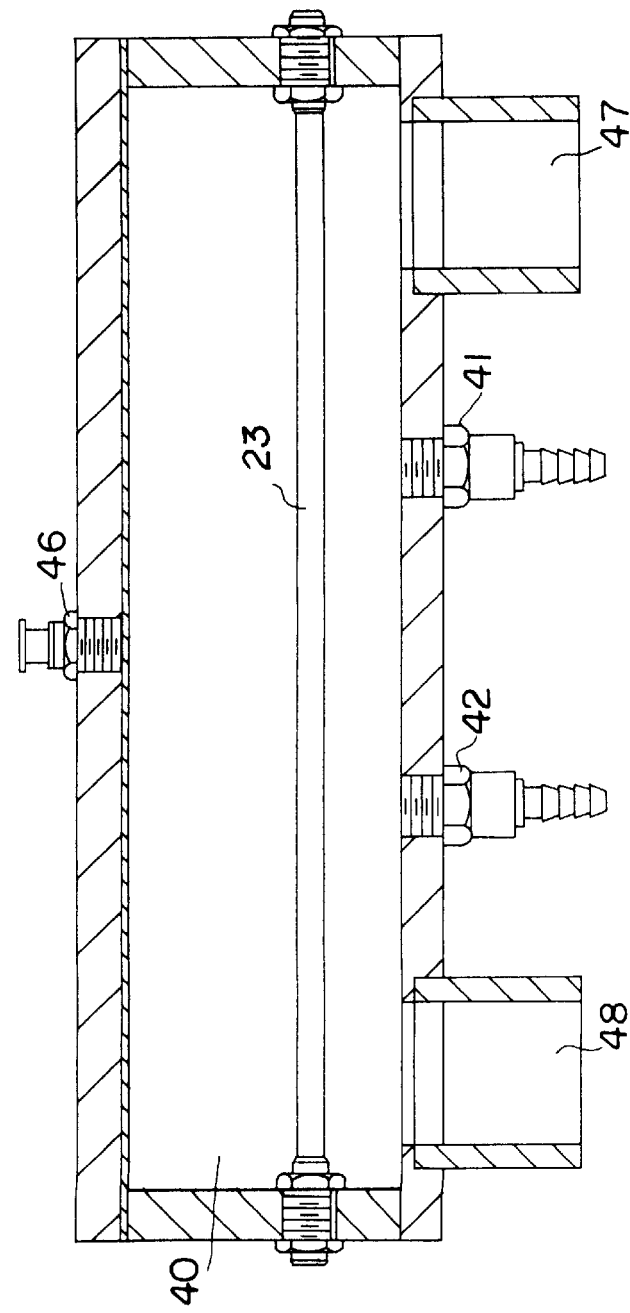

CARDIOVASCULAR BIOREACTOR APPARATUS AND METHOD

CROSS REFERENCE TO RELATED APPLICATIONS

This application is a continuation of U.S. patent application Ser. No. 08/796,573 filed on. Feb. 6, 1997, now U.S. Pat. No. 5,916,800, which is a continuation of U.S. patent application Ser. No. 08/482,990 filed on Jun. 7, 1995, abandoned.

TECHNICAL FIELD

The invention involves a method and apparatus for processing biological material.

BACKGROUND OF THE INVENTION

Surgical implantation of tissue is utilized to replace and/or repair human tissues. For example, hereditary defects, disease, and/or trauma may damage tissues such that replacement and/or repair is desirable. These implantable tissues may be provided by individual human donors. However, because of the scarcity of appropriate human donors, non-human tissues have been increasingly employed instead. Such biological tissues have been used to replace heart valves, ligaments, tendons and skin, among other tissues.

Care must be taken in preparing, manufacturing, storing, and shipping these replacement materials. While many have focused on the design and construction of the replacement materials themselves, fewer have focused on the structures that would aide in constructing, evaluating, and storing biological material such as heart valves and vascular grafts.

For example, some devices or methods have tried to accomplish the culturing under subphysiologic conditions. There is a need for a system and apparatus for evaluating biological material under normal and supra-physiological conditions. Some of this need is represented by a need to modify the current pulse duplicator and accelerated life testers.

Furthermore, testing and monitoring methods and devices are typically not conducted in sterile and aseptic conditions. Mounting the fixture in a sealable chamber for use in storage and shipping has not been accomplished. There is a need to provide a system and apparatus that provides a sterile environment throughout the construction, testing, and storage stages. This need extends to providing a test and evaluation container that also may be used as a storage and shipping container.

Furthermore, the design of some of the equipment for working with biological material, such as the mandrels for working with heart valves and vascular grafts, are sometimes awkward to use and do not adequately address the problems of the entire manufacturing process. For example, a single valve mounting and release system has not been accomplished. There is a need to provide a new mounting system for biological materials.

SUMMARY OF THE INVENTION

The present invention provides a method, apparatus, and system to process and ship biological products, typically cardiovascular products, within a single sterile, aseptic system and apparatus.

The present invention also provides an integral system and apparatus to process biological materials, such as heart valves and vascular grafts.

The present invention also provides a processing chamber that may also be used as a storage and/or shipping container.

This single system provides culturing, monitoring, testing, and storage capabilities in a minimum amount of space, and has the capability of providing multiple tasks and multiple products.

The system according to the invention includes a biological material processing chamber, an environmental control circuit, a nutrient supply circuit, and a pulse evaluation unit.

The methods and devices according to the present invention have the added advantage of relatively low costs in time, effort, personnel, and equipment required to process, evaluate, store, and ship biological material(s).

BRIEF DESCRIPTION OF THE DRAWINGS

FIG. 2A is a sectional top view of an exemplary embodiment of first compartment 40 according to the invention.

FIG. 2B is a sectional side view of first compartment 40 of FIG. 2A.

SPECIFIC DESCRIPTION OF THE INVENTION

Figure 1:
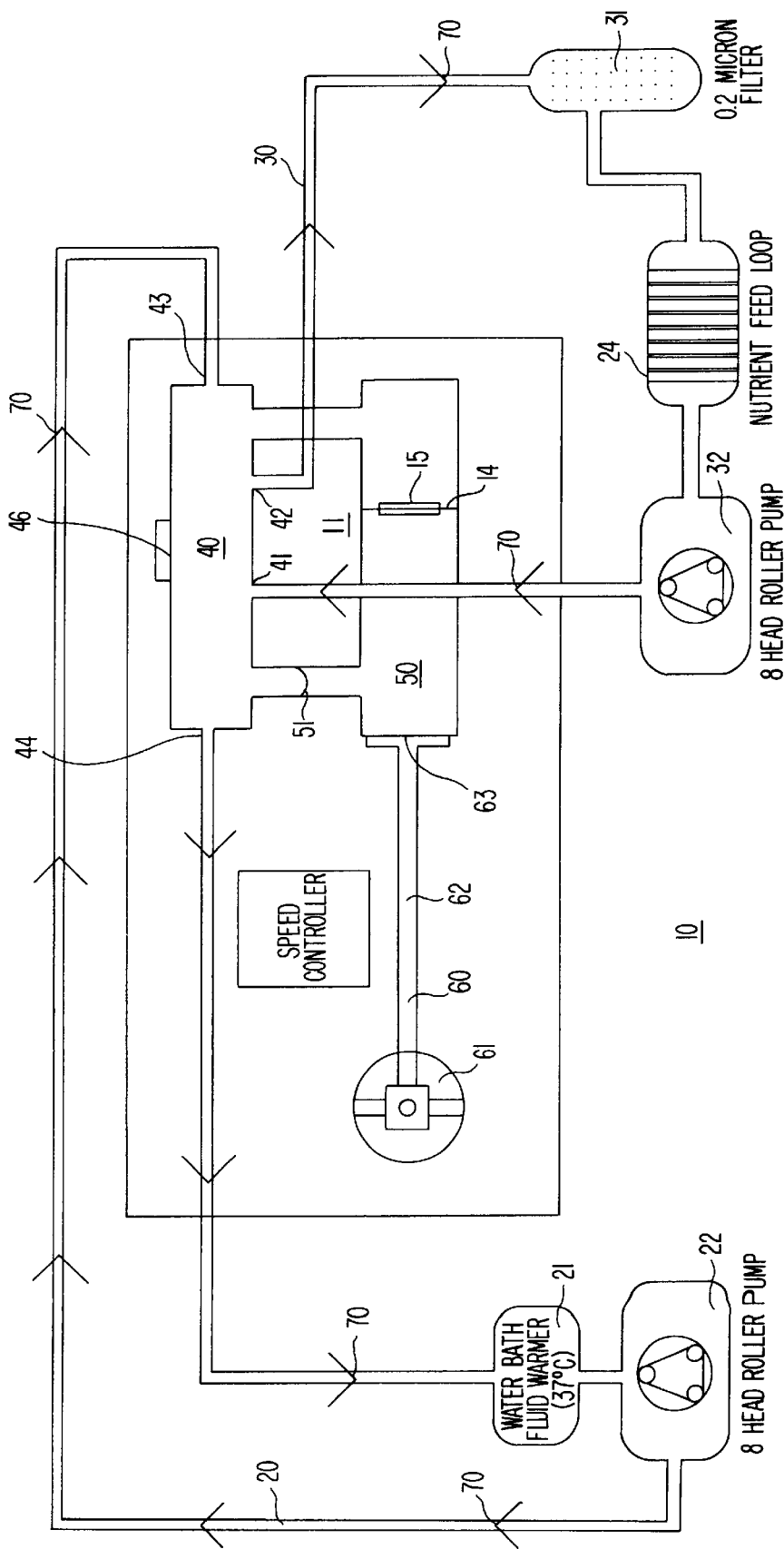
FIG. 1 is an embodiment of a system according to the invention.

The system according to the invention includes a biological material processing chamber, an environmental control circuit, a nutrient supply circuit, and a pulse evaluation unit.

The present invention also includes a biological material processing, evaluation, and storage system comprising a chamber for processing, evaluating, and storing a predetermined biological material, such as one or more heart valves; a temperature circuit in fluid communication with the chamber; and a nutrient supply circuit in fluid communication with the chamber. This system may also include a pulse evaluation circuit.

Processing, as used herein, refers to all of the various steps in constructing and preparing biological material for implantation, from the initial construction protocols to storing and shipping the prepared implant. Processing also includes testing and evaluating biological material, such as heart valves, including testing and evaluating new designs.

The invention allows the sterile mounting, culturing, monitoring, and functional evaluation of biological material, such as heart valves and/or vascular grafts, within a single chamber/system at various physiological conditions, i.e., below, at, or above normal physiologic conditions.

The present invention also comprises an apparatus for processing and storing biological material comprising a chamber having a first compartment incorporating an environmental control flow path and a nutrient feed flow path, and a second chamber for evaluating the biological material, the second chamber including a mount suitable for mounting and testing the biological material.

The present invention also comprises a method for processing biological material comprising fixing a biological material to a suitable mount, exposing the biological material to predetermined evaluation conditions, ending the evaluation conditions, and storing the biological material in the chamber. The method according to the invention may also include exposing the biological material to a nutrient feed, and may further include controlling the environmental conditions within the system. The method may include sealing the biological material in its processing chamber, and may further include shipping the sealed biological material in the same processing chamber.

As used herein, biological material refers to any cellular matter for which it may be desirable to form into a predetermined shape, to evaluate, and to store. Typically "biological tissue" refers to a collagen-containing material which may be derived from different animal species, typically mammalian. Suitable sources include, but are not limited to, bovine, porcine, equine, ovine, kangaroo, rabbit, boar, bear, and human.

The biological material is typically a soft tissue suitable for implantation, such as bioprosthetic tissue or the like, but the invention should not be limited thereby. Specific examples include, but are not limited to, heart valves, particularly porcine heart valves; aortic roots, walls, and/or leaflets; pericardium, preferably bovine pericardium or the like, and products derived from pericardium, such as a pericardial patch; epithelial of fibrous connective tissue derived materials such as *dura mater, fascia lata,* amnion, cartilage, and the like; homograft tissues, such as aortic homografts and saphenous bypass grafts; tendons; ligaments; skin patches; blood vessels, particularly bovine arteries and veins, and human umbilical tissue, such as veins; bone; and the like. The biological material may also include segments, portions, or parts of any of the materials noted above. Any other biologically-derived materials which are known, or become known, as being suitable for processing in accordance with the invention are within the contemplation of the invention.

For the purpose of some embodiments of the invention, the term biological material will also encompass synthetic and/or mechanical material which are sometimes used to reinforce, substitute, or replace collagen-containing materials. For example, heart valves may be wholly natural porcine heart valves, but they may also include polymeric or synthetic structures, or they may wholly comprise synthetic materials, such as metal, polymers, thermoplastics, fabric, and the like. The use and structure of these synthetic/mechanical structures are well known, and are included within the invention.

Figure 3:
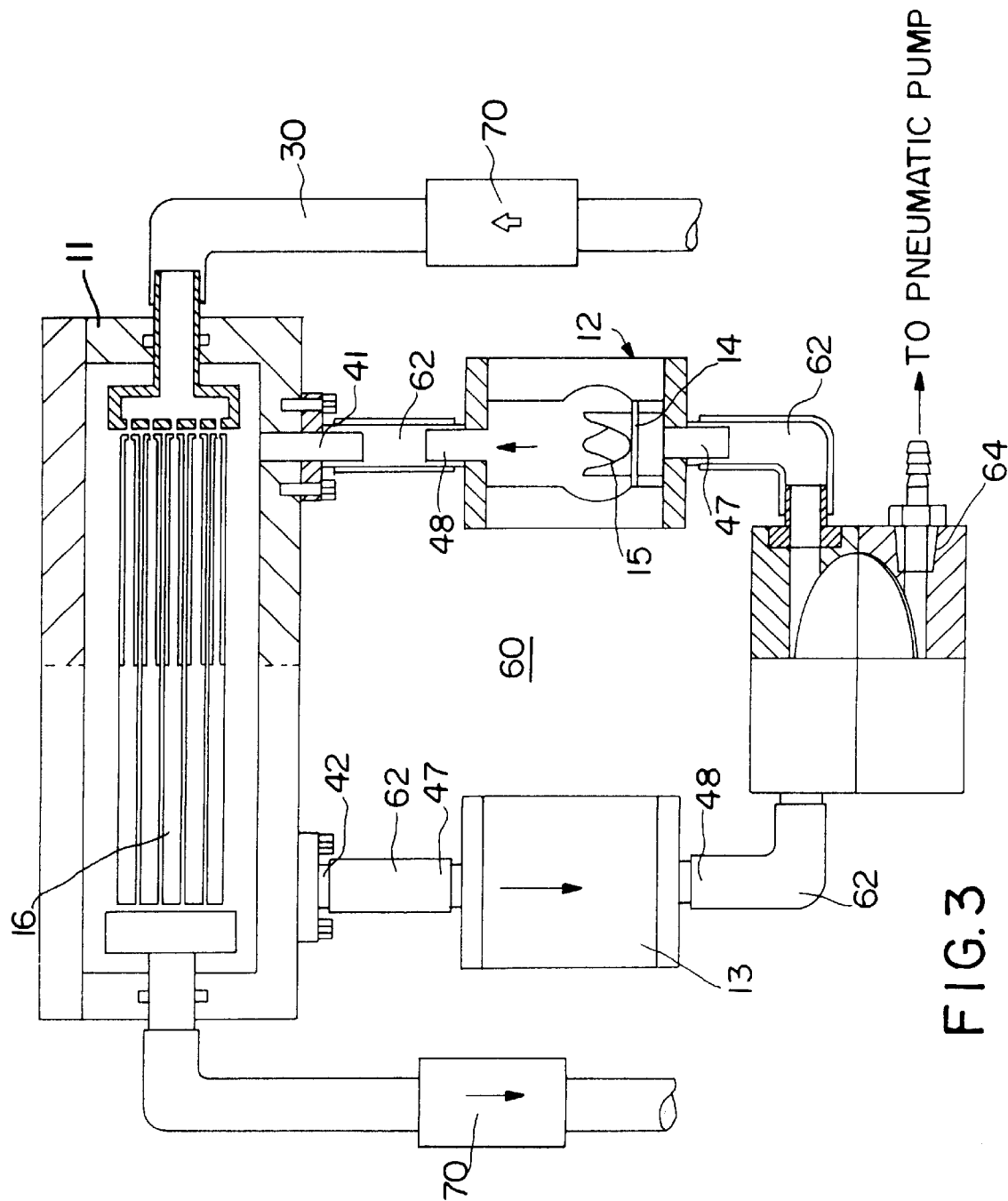
FIG. 3 is an exemplary embodiment of second compartment 50 according to the invention.

Exemplary processing systems according to the invention are shown in FIGS. 1–3. For example, system 10 may include a processing chamber 11, environmental control circuit or flow path 20, nutrient supply circuit or flow path 30, and, optionally, pulse evaluation unit or flow path 60. In a preferred embodiment of the system, the system is an integral or unitary system, even more preferably, with at least one removable chamber 12/13 also suitable for storing and/or shipping the biological material (see FIG. 3).

The processing chamber 11 is a container, housing or the like for processing and storing the biological material. The chamber may be of different configurations, as dictated and found desirable for a particular biological material. In some embodiments of the invention, the same chamber may be used to construct, test and evaluate, store, and ship the biological material. In the preferred embodiments of the invention, chamber 11 is used to process the biological material, except for storing and/or shipping.

Releasable chambers 12 and 13 is a container, housing or the like for processing the biological material. The chamber may be of different configurations, as dictated and found desirable for a particular biological material. Chambers 12 and 13 typically include a mount 14 or the like for positioning the biological material in the proper position for testing, evaluating, constructing, storing, and/or shipping. In a preferred embodiment of the invention, chambers 12 and 13 may be sealed and/or released from the system, e.g., by heat sealing the inlet and the outlet of the releasable chamber, or by sealing a portion of the conduit upstream and downstream of the chamber.

As will be explained in more detail below, it will be appreciated that should it be desirable to process only one biological material in a processing circuit, one of releasable chambers 12 and 13 may be a check valve or the like. In this embodiment of the invention, chamber 12 or 13 would not need to be releasable or sealable.

Figure 4:
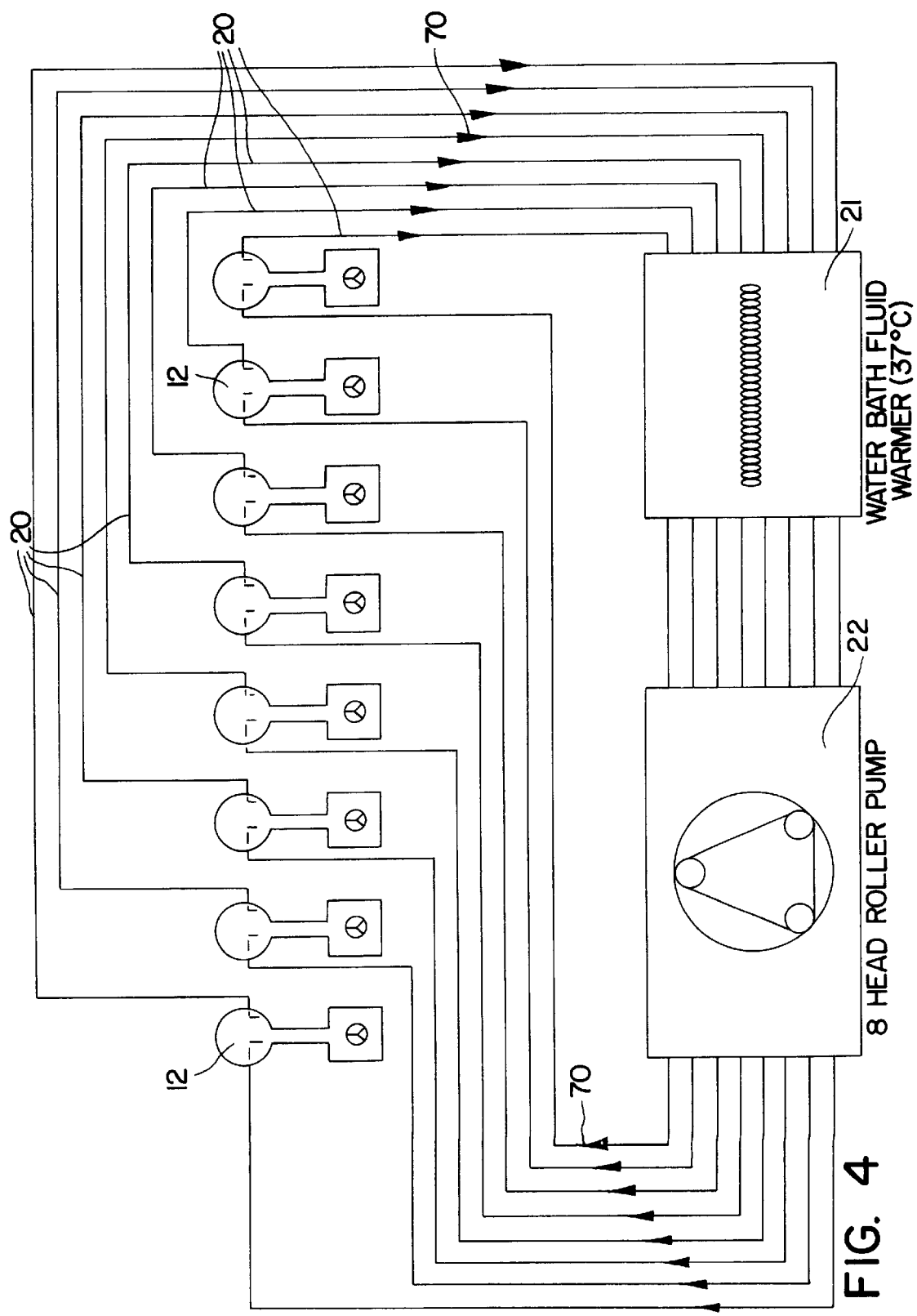
FIG. 4 is an exemplary embodiment of an environmental control circuit according to the invention.

The environmental control circuit 20, shown in FIGS. 1 and 4, is in fluid communication with chamber 11, and provides temperature control to the system 10 or parts of the system. This circuit 20 may be variously configured, and typically includes a pump 22, a first heat exchanger 21 to regulate the temperature of the fluid passing through it, and a second heat exchanger 23 (see FIG. 2), preferably in the chamber 11, to regulate the temperature of the chamber 11, any fluids or nutrient solutions, and the biological material. Also, the environmental control circuit 20 may be used to alter the temperature of the system 10, or parts of the system, when evaluating the biological material under predetermined stress or accelerated life conditions.

Alternatively, the environmental control circuit 20 may include one or more flow paths or individual circuits. The exemplary embodiment illustrated in FIG. 4 shows eight circuits, but any number of circuits may be used. It is intended that the invention is not to be limited by the number of environmental control circuits.

Figure 5:
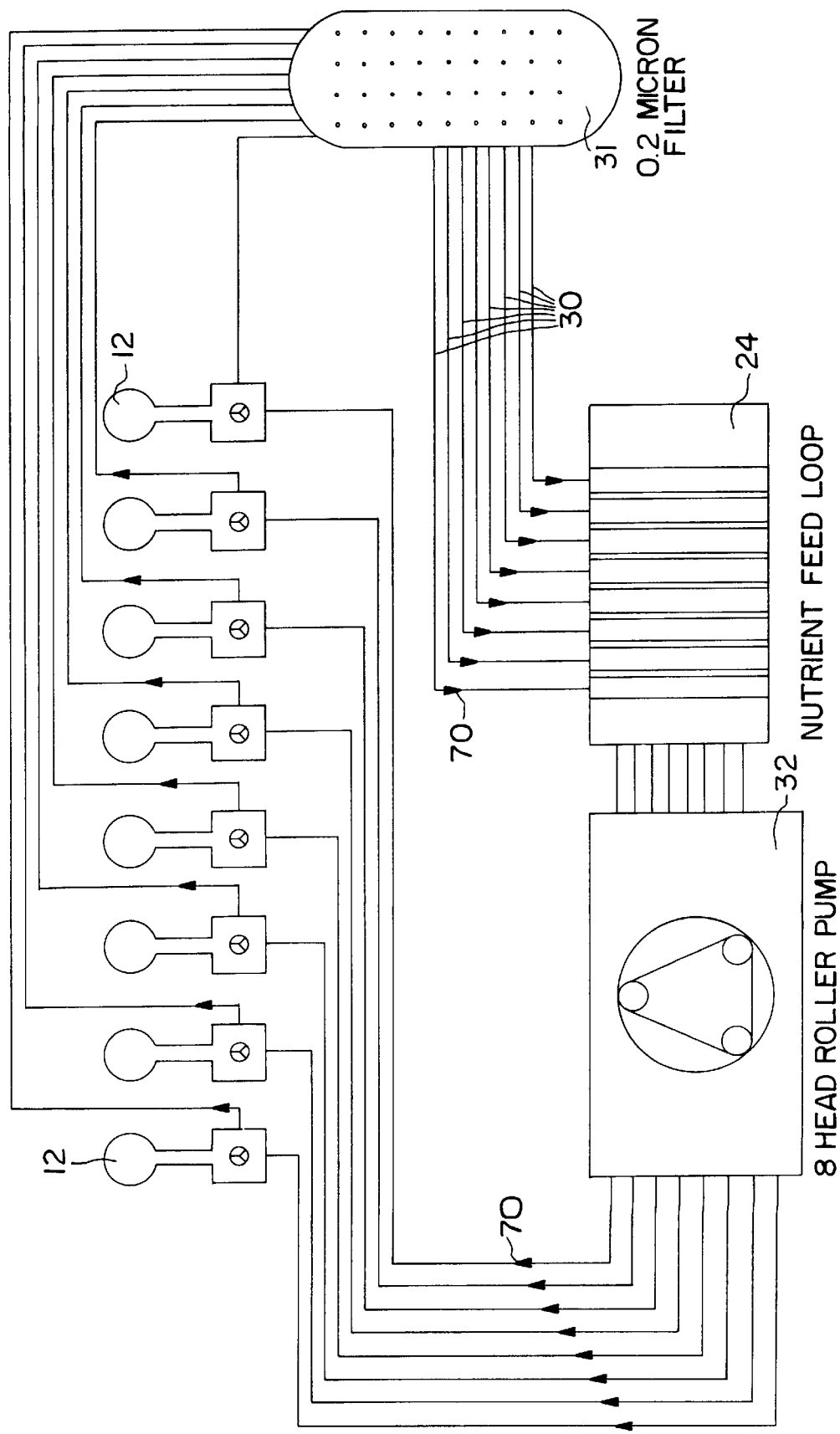
FIG. 5 is an exemplary embodiment of a nutrient feed circuit according to the invention.
Figure 6:
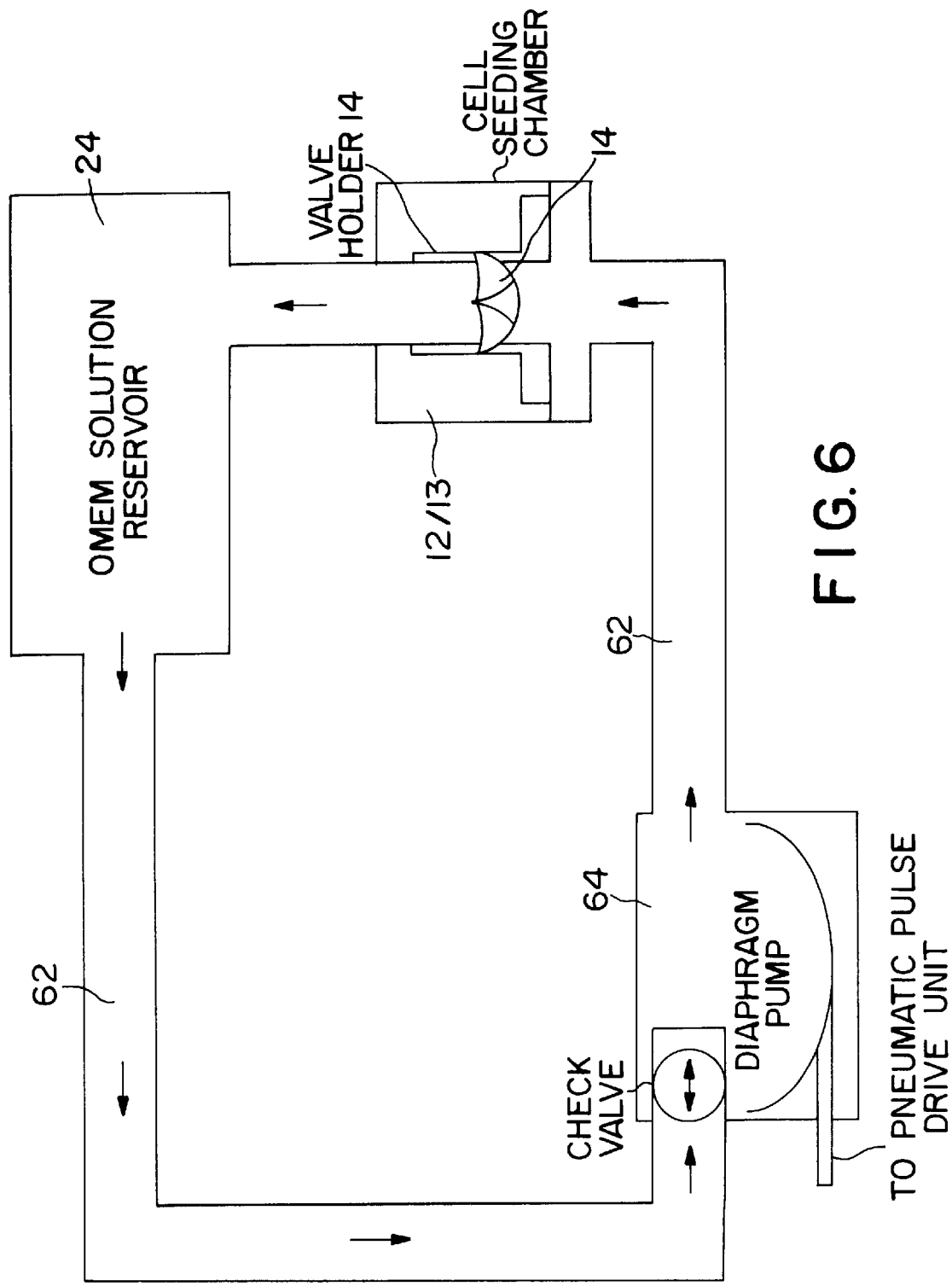
FIG. 6 is an alternative embodiment of a pulse evaluation unit according to the invention.

The nutrient supply circuit 30, shown in FIGS. 1 and 5, is in fluid communication with the chamber 11, and provides nutrients and the like to maintain, sustain, and optionally, promote the growth of the biological material. The content and configuration of the nutrient supply circuit may be variously configured for a specific biological material and for a particular need, as is explained in more detail below.

Alternatively, the nutrient supply circuit 30 may include one or more flow paths or individual circuits. The exemplary embodiment illustrated in FIG. 5 shows eight circuits, but any number of circuits may be used. It is intended that the invention is not to be limited by the number of nutrient supply circuits.

The pulse evaluation circuit 60 is used to process the biological material in a pre-determined manner. For example, circuit 60 may be used to evaluate the function, durability, and design of a biological material, such as a heart valve. In one embodiment of the invention, the pulse evaluation circuit 60 tests one or more heart valves under conditions similar to the conditions the valve will be subjected to after implantation. The pulse evaluation unit may also be used to test and evaluate new heart valve designs.

In accordance with the invention, the pulse evaluation circuit 60 may include various components and may be variously configured. For example, the pulse evaluation circuit shown in FIG. 1 is in fluid communication with second compartment 50 of chamber 11. This exemplary circuit includes a motor 61, pump, or the like for alternatingly producing pressure and a vacuum; a conduit 62 for establishing fluid communication with chamber 11; and a diaphragm 63 or the like interposed in the circuit 60 between the motor 61 and an inlet of chamber 11. In the illustrated embodiment, the diaphragm forms a portion of the inlet into chamber 11.

An alternative configuration of pulse evaluation circuit 60 is illustrated in FIG. 3. In this exemplary embodiment of the invention, the circuit 60 includes a pneumatic pump 64 or the like, in fluid communication with chamber 11 through conduit 62. The flow path into and out of chamber 11 may be through inlet 41 and inlet 42 (part of the nutrient supply circuit), or may through its separate inlet and outlet (not shown). One or more chambers 12 and 13 may be interposed in conduit 62 between the pump 64 and the chamber 11. As illustrated in FIGS. 4 and 5, the pulse evaluation circuit may comprise in part the nutrient supply circuit (FIG. 5) and/or the environmental control circuit (FIG. 4). In an exemplary embodiment partially illustrated in FIG. 4 and 5, the pulse evaluation circuit may include more than one flow path or circuits. FIGS. 4 and 5 shows eight circuits, but any number of circuits may be used. It is intended that the invention is not to be limited by the number of pulse evaluation circuits.

As noted in more detail below, the individual parts which constitute a biological material processing assembly 10 may vary according to its intended use. For example, it may be desirable to test and evaluate the competency of a biological material, such as a heart valve. It may also be desirable to seed a biological material, such as a vascular graft or a heart valve. It may be further desirable to provide nutrient and environmental control systems. These and other uses will be explained in more detail below.

Any number and combinations of assemblies, filters, containers, pumps, and conduits are suitable. One skilled in the art will recognize that the invention as described may be reconfigured into different combinations.

In accordance with the invention, the conduits, assemblies, filters, and containers which constitute a biological fluid processing assembly may be arranged to define different flow paths. Since independent flow paths may be present, included within the scope of the present invention is the concurrent or sequential passage of separate fluids through the biological material processing assembly.

Individual components of a processing system according to the invention will now be described.

The Chamber

A processing and evaluation chamber according to the invention may be variously configured. The chamber will typically include a housing having at least one compartment, and the housing will typically have at least one inlet and at least one outlet. In some preferred embodiments of the invention, the chamber will include a mount for positioning and retaining a biological material.

For example, FIG. 1 shows a two-compartment chamber 11. FIG. 3 shows a one-compartment chamber 11. In the various configurations of the chamber, there may be included one or more nutrient flow paths, one or more environment control flow path, and one or more pulse evaluation flowpaths.

For example, in the configuration illustrated in FIG. 1, chamber 11 includes a first compartment 40 having a first inlet 41 and a first outlet 42 for providing a nutrient flow path through the chamber. The chamber 11 may also include a second inlet 43 and a second outlet 44 for providing an environmental control flow path through the chamber 11. In a preferred embodiment first compartment 40 includes a heat exchange tube 23 (FIG. 2). The heat exchange tube 23 may be variously configured, and in the preferred embodiment, the tube 23 (FIG. 2) has a serpentine configuration within the chamber.

In another example, in the configuration illustrated in FIG. 3, system 10 includes a chamber 11 having one compartment in fluid communication with at least one of a nutrient supply circuit and an environmental control circuit. In this embodiment of the invention, chamber 11 may also include a pulse evaluation circuit 60. In the illustrated configuration, pulse evaluation unit 60 is in fluid communication with chamber 11 through inlet 41 and outlet 42.

The housing or chamber 11 may have a variety of configurations. Exemplary configurations are shown in the Figures.

As noted above, in accordance with the invention, the biological material may then be placed or packaged in a container 12. In a preferred embodiment of the invention, the processed biological material is surrounded by nutrient solution when it is sealed and shipped. If seeding or the presence of cells in the nutrient fluid is not desirable, the biological material may be sealed and shipped in physiological saline or the like. Packaging preferably means placing in a container suitable for storage and/or shipping.

The container 12/13 or chamber 11 may be constructed of any material compatible with a nutrient solution and capable of withstanding sterilization, e.g., by electron beam, gamma radiation, autoclave, acetylene oxide, or the like. In a preferred embodiment, the chamber 11 or container 12/13 is formed of glass or polymeric plastic. Suitable plastic materials include polyethylene; acrylates such as polymethyl methacrylate and polymethyl acrylate; polymethyl pentene-1; polyvinyl chloride; vinyl chloride-vinylidene chloride copolymers; polypropylene; urea-formaldehyde copolymer; melamine-formaldehyde copolymer; polystyrene; polyamide; polytetrafluoroethylene; polyfluorotrichloroethylene; polycarbonates; polyesters; phenol-formaldehyde resins; polyvinyl butyryl, cellulose acetate; cellulose acetate propionate; ethyl cellulose; polyoxymethylene; and polyacrylonitrile. In a preferred embodiment, the container is constructed of polypropylene, polyethylene, and/or epoxies. It is intended that the invention should not be limited by the type of container and seal being employed; other materials may be used, as well as mixtures, blends, and/or copolymers of any of the above.

Any housing, container, or chamber in a system of the invention also preferably includes a transparent portion positioned to permit observation within the chamber. For example, the transparent portion may be a window in a cover or wall. Alternatively, the entire housing may be formed from a transparent material, such as a transparent plastic.

Environmental Control

Although the environmental control circuit may be variously configured, the illustrated environmental control circuit 20 comprises a heat exchanger 21 and a pump 22 in fluid communication with the chamber 11. In some embodiments of the invention, the environmental control circuit 20 may include an arrangement of separate structures and flow paths, each providing separate fluid communication with the chamber and/or an individual biological material.

Nutrient Supply

Although the nutrient supply circuit may be variously configured, the illustrated nutrient supply circuit 30 comprises a filter 31 and a pump 32 in fluid communication with the chamber 11. The nutrient supply circuit 30 may also include a source of nutrient solution, a fill port, and a drain (not shown).

In accordance with the invention, the nutrient solution may be a variety of solutions, as pre-determined for a particular purpose. For example, the nutrient solution may be physiological saline, typically used to maintain, store, and/or ship the biological material. In other embodiments of the invention, the nutrient solution, such as the well known and commercially available OMEM solution, contains nutrients, vitamins, minerals, antibiotics, and the like. In accordance with some embodiments of the invention, this solution, or a nutrient solution like it, will also include cells suitable for seeding a biological material, such as a heart valve or a vascular graft. It is intended that the invention is not to be limited by the type or content of nutrient solution passing through the circuit 30.

As used herein, physiologically acceptable fluid refers to any fluid or additive suitable for contacting biological material. The physiologically acceptable fluid may also include nutrients and the like. Exemplary physiologically acceptable fluids include but are not limited to preservative solutions, aldehyde solutions, saline solution, an isotonic (about 0.9%) saline solution, or about a 5% albumin solution or suspension. It is intended that the present invention is not to be limited by the type of physiologically acceptable fluid used.

Pulse Drive Unit

In some embodiments of the invention, the system 10 may include one or more biological material evaluation units or circuits. For example, in the illustrated embodiment, biological material such as heart valves may be evaluated using a pulse evaluation circuit 60. The pulse evaluation circuit may be variously configured. An important feature of the pulse evaluation circuit 60 is a pneumatic portion 61 for testing the competency of one or more heart valves. The pneumatic portion may include structures for regulating pressure and structures for establishing a vacuum. The unit 60 may also include a timing circuit, preferably a solid state timing circuit, and may include fixed and/or variable timing controls.

In a preferred embodiment of the invention, the pulse evaluation circuit 60 provides timed pulsatile compressed air and vacuum to a suitable diaphragm pump via a three way diverter valve (not shown) actuated by the timing circuit.

Pressure Differential Generator

A system according to the invention may comprise a pressure differential generator e.g., a pump or the like, which is suitable for inducing fluid flow from chamber 11 to other parts of the system, or inducing flow from other parts of the system to chamber 11. The pressure differential generator is operatively associated with a biological material processing assembly, an example of which is shown as 22 and 31 in FIG. 1. The pressure differential generator may also be operatively associated with one or more fluid flow paths within the system 10, or with one or more structures within a circuit.

Movement of fluid through the system is effected by maintaining a pressure differential between the chamber and the destination of the fluid (e.g., a filter or a temperature control unit). Exemplary means of establishing this pressure differential may be by a mechanical member bearing directly against a fluid-collection container, mechanical expressor, gravity head, applying pressure to the collection bag by hand or with a pressure cuff, or by an in-line pump.

Filters

The filter 31 is chosen so that the sterility of the system is not compromised. The filter 31 is particularly suited for use in closed systems. Embodiments of the present invention may be used preferably with a sterile fluid, such as a biological fluid. A sterile fluid is one which is substantially free of viable contaminating microorganisms. Systems according to the invention may define a fluid communication path wherein the fluid is maintained free of viable contaminating microorganisms, or the sterility of the fluid is not adversely affected by the passage of the fluid through the assembly.

A variety of filters may be used, provided the requisite properties of the particular porous medium are achieved. These include the necessary strength to handle the differential pressures encountered in use and the ability to provide the desired permeability without the application of excessive pressure. In a sterile system, the porous medium should also preferably have a pore rating of about 0.2 micrometer or less to preclude bacteria passage.

Freedom from contaminants refers to a relative amount of contaminants and is variously defined according to a specific industry, fluid and/or intended use. For example, a biological fluid which is substantially free of contaminants is considered free of viable microorganisms, and is typically referred to as "sterile".

Automated Control Arrangement

In accordance with the invention, an automated control arrangement, in response to predetermined conditions, may send and receive signals, and control the overall sequence and flow of fluid or gas from one portion of the system to another. The control arrangement may be connected to the various elements of the system, and may include one or more connections to a container, to a conduit, to a specific element in the biological material processing assembly or the pressure differential generator, to a valve, or the like.

For example, the automated control arrangement may include one or more devices, switches, and/or indicators or monitors to achieve a desired purpose, including, but not limited to: a power switch; a start switch; a stop switch; a sequence selection switch; weight sensor devices, switches, and/or indicators; time sensor devices, switches, and/or indicators; optical sensor devices, switches, and/or indicators; and fluid flow sensor devices, switches, and/or indicators.

It is intended that each of these sensors monitor a predetermined condition, and react or provide feedback according to a predetermined or pre-set array of variables.

Preferably, the pressure regulating mechanism, such as that shown as 64 in FIG. 3, may include a four way pneumatic valve capable of connecting a flexible hose to the input or to the output of a standard piston pump. The pneumatic valve may be electronically controlled by the control unit. Additionally, there may be a plurality of relief valves and a pressure sensor electronically controlled and monitored by the control unit. In this manner, the control unit may control and monitor the pressure or vacuum exerted on the pulse evaluation circuit.

As noted above, the invention may include a variety of other configurations and assemblies. Some of these variations will now be described.

As with all illustrated embodiments herein, a number of variations in the illustrated constructions are envisioned.

Each of the assemblies or containers may be in fluid communication through conduits, typically flexible tubing, and preferably plasticized PVC. A seal, valve, clamp, pinch clamp, or transfer leg closure or cannula may also be positioned in or on the tubing or in or on the chamber. In accordance with the present invention, the assemblies, containers, and conduits may be previously connected in a closed, sterile manner, or segments of the system may be inserted into a closed system in a sterile manner.

As used herein, adapted for communication refers to any means or methods for establishing fluid flow through the system. For example, two conduits may be heat sealed together, to form a sterile connection using known connection devices; or a conduit may have a connector adapted to receive or connect to a mated connector on another conduit; or the connector may be a spike, adapted to be inserted in a fluid container, such as a nutrient-containing bag or the like. As used herein, connector refers to any structure used to form a joint or to join itself to another piece. These connectors establish a flow path through various elements of an assembly or system. Connector, as used herein, typically refers to penetrating connectors, such as a spike, cannula, or needle; and mating connectors, such as Luer-type, screw-type, friction-type, or connectors which are bonded together. It is intended that the present invention is not to be limited by the type of connector or connection used for establishing fluid flow through the conduit.

A flow control device, such as a seal, valve, clamp, pinch clamp, roller, transfer leg closure, or the like is typically located in or on the tubing and/or containers. In accordance with the invention, a flow control device may be positioned on or in any or all of the conduits in order to facilitate a desired function, i.e., establishing a desired flow path for a fluid or gas. It is intended that the present invention should not be limited by the number, placement, or use of such flow control devices.

Other variations are also envisioned. For example, where the connector and fluid conduit comprise separate components, they could be connected by a variety of other means, e.g. mating threaded fittings. Alternatively, a bracket may be attached to a sleeve, either formed integrally with the bracket or otherwise connected thereto. This sleeve may be connected to a section of tubing through telescopic engagement, i.e. a coaxial friction fit wherein one member is inserted within the other, with friction between the two members retaining the coupling. In another variant construction for the female connector, the two bores and the tubing can be variously configured. Alternatively, they may be formed with cross sections of various geometries, for example rectangular or elliptical.

As used herein, seeding refers to contacting the surface of a biological material or a synthetic substrate with cells under conditions in which the cells bind or stick to the surface and grow. For example, contacting a heart valve or a vascular graft with a cell-containing nutrient solution allows or encourages the cells to proliferate on the surface of the valve or graft.

In a typical seeding or tissue engineering protocol, a form or the like is positioned or fixed in the container and the nutrient solution containing cells is directed against the form. The cells adhere to the form, and are maintained and proliferate due to pre-determined ingredients in the nutrient solution.

One skilled in the art will appreciate that the form may be a synthetic or biological form or matrix, or the form may be a heart valve or vascular graft itself.

As noted above, the releasable chamber 12 and 13 may be sealed and used for storing and/or shipping the biological material. Any method or structure for sealing the chamber may be used. For example, a portion of the conduit on the inlet and the outlet side of the chamber may be heat sealed or permanently clamped.

In accordance with one aspect of the invention, flow through a circuit is preferably maintained in one direction. The flow path may be maintained by the application of pressure, e.g., using one of the previously described pumps. One or more of the fluid pathways may also include one or more valves or flow restrictors, such as a check valve, to prevent the fluid from reversing direction. In some embodiments of the invention, it may be desirable to use the biological material itself as a check valve, e.g., a heart valve, which in its natural function, permits fluid flow in one direction. For example, to establish a circular flow path in FIG. 3, fluid flow may pass through biological material in chamber 12, through chamber 11, and through chamber 13. Fluid may be prevented from reversing direction by substituting a check valve for chamber 13, or chamber 13 may include a heart valve.

In accordance with another aspect of the invention, a system may include one or more compliant structures. In a preferred embodiment of the invention, these compliant structures act as a volumetric reservoir to temporarily hold the fluid. After a pre-determined condition (e.g., amount of time or pressure build-up), the compliant structure will then release the collected fluid. Exemplary compliant structures include but are not limited to flexible bags or flexible containers, and may even include biological material, such as vascular graft material. For example, FIG. 3 shows vascular graft material 16 positioned in chamber 11 across or in the nutrient fluid flow 30. The vascular graft material retains the nutrient solution until a pre-determined portion of the processing cycle, e.g., pneumatic pump changing cycle from pressure to vacuum.

In accordance with the invention, these compliant structures may be positioned anywhere in the system, including those noted above. Compliant structures 51 could also be positioned between the first compartment 40 and the second compartment 50, as shown in FIG. 1.

In FIG. 3, biological material 15 is preferably positioned in chamber 12 near inlet 47. Since it may be desirable to establish a circular flow path between chamber 11 and pump 64, biological material 15 needs to be positioned near inlet 47 of chamber 13.

In accordance with the invention, processing a biological material may include processing more than one of the same type of biological material, or more than one of different types of biological material. For example, FIG. 3 illustrates the simultaneous processing of a biological material 15, such as a heart valve, and a biological material 16, such as a vascular graft.

Diaphragm or pneumatic pump 64 functions by forcing a compliant membrane or balloon-like structure within the housing of the pump against a conduit or fluid flow path that runs through the housing. When air is pumped into the balloon, it expands and presses against the conduit, forcing any fluid in the conduit toward container 12 and container 13. In container 12, the biological material or check valve is oriented so that the fluid will pass through the chamber 12 and into chamber 11. In container 13, the biological material or check valve is oriented so that fluid passing into chamber 13 from the pump side of the circuit will close the valve. Conversely, when pressure in the pump is released by releasing air in the balloon, the lack of pressure will close the valve in container 12 and allow the valve in chamber 13 to open. Such alternating processes simulate the conditions found in the human heart, e.g., a normal physiological condition. By modulating or changing the speed, pressure, and/or temperature of the process, such alternating processes may also be used to test the durability or design of a specific biological material, among other characteristics that can be tested. As will be appreciated by one skilled in the art, the simulated beat rate cardiac flow rate, and the cardiac pressure, i.e., the physiological conditions, may be modified for a pre-determined purpose. For example, it may be desirable to manufacture a biological material at below physiological conditions (e.g., about 0–50 bpm, beats per minute), test the biological material at physiological conditions (about 70 bpm), and evaluate the durability of the biological material above physiological conditions (about 1000 bpm, or the equivalent of 5 years can be tested in 3 days). This and other variations of the same theme are contemplated by the invention. A more detailed description of the cycling process can be found in the Examples.

Any type of diaphragm pump may used in the system of the present invention. For example, any device providing a piston driving force, or a bladder, may be used, as long as the fluid contact material is sterilizable.

The embodiment of the invention illustrated in FIG. 1 also shows other optional features of the invention. A tank 24, container, or the like may provide a source of nutrient solution. In an embodiment of the invention, the tank 24 may also serve as a manifold for separating or establishing multiple fluid flow paths, such as those shown in FIG. 5.

Another optional feature of the invention includes positioning one or more flow restrictors, clamps, or valves in order to direct or control fluid flow. For example, in FIG. 1, the channels, pathways, or conduits between the first compartment and the second compartment may include valves, such as check valves, to maintain a circular flow path between the compartments. Other exemplary check valves are shown as check valve 70.

EXAMPLES

All equipment should be sterilized before use and aseptic conditions will be maintained throughout the cycling period.

Example 1

The test system will be a self-contained loop with a compliant fluid reservoir which may be constructed of vascular graft material and two check valves which will utilize the natural function of two opposing heart valves. The system will be constructed of polycarbonate material for easy sterilization and monitoring. The system will be driven by a pneumatic system which will have a polyurethane fluid contacting surface. With proper fluid (nutrient) volume and adjustable graft compliance, the system will be able to operate below, at, or above physiologic cardiovascular pressures and flow and beat rates. A single pneumatic pumping system will have the capability to drive multiple valves and sets of grafts. The valve itself will have a single mount and release mechanism for easy manipulation (since there is no supporting structure). The valve mounting chamber will have the capability of being sealed upon removal from the pumping system and used as the storage and shipping container.

Example 2

Bioreactor Evaluation Equipment
1. Design #1: (to be used for valve evaluations and cell seeding)
Modification of current single chamber accelerated life testers
Two piece design: valve is mounted within flow loop under a hood and flow loop is connected to drive shaft.
Test fluid is nutrient rich and will be volumetrically removed and infused into the test chamber through layered filtration.
The valves will be dynamically cycled at rates ranging from physiologic (70 BPM) to durability stages (1000 BPM).
All equipment will be sterilized before use and aseptic conditions will be maintained throughout the cycling period.
The system can be examined for bacterial intervention through the staged filter system or by directly sampling fluid medium.
Each system will be fed from a separate fluid reservoir to ensure that a mishap in one valve will not effect the environment of others.
A single fluid infusion and removal pump will have the ability to operate 8 systems.

Example 3

Design #2: (to be used for cell seeding)
A six valve design that incorporates a single pumping mechanism to drive the system.
Each valve will be mounted in a separate sealable chamber which will be mounted to the system.
The valve can be cycled at rates and conditions ranging from near zero up to physiologic (0–200 BPM), or above (about 1000 bpm).
The nutrient rich fluid will be volumetrically infused and removed through a staged filter design.
Upon completion of the reactor time the chamber will be sealed and removed from the cycling system.
The valve will be contained in the sealed chamber with fresh nutrient fluid and stored and shipped as such.
Valve conditions (bacteria present) can be monitored through the staged filtration system or by direct sampling of the fluid.

Example 4

The pneumatic section of the Pulse Drive Unit is a closed loop system. Compressed air is supplied to the pneumatic circuit via a 3 way solenoid valve. The solenoid valve is connected to the input port of the pressure regulates that controls systolic output pressure. The solenoid is activated when the power switch is moved to the ON position. When the power is turned OFF, the compressed air supply is shunted to atmosphere through a snubber.

This allows the pneumatic circuit to unload between runs. Control of systolic pressure is achieved with a pressure regulator and reservoir. Diastolic pressure is supplied via an internal vacuum/compressor pump. Control of both positive and negative diastolic pressure is achieved with a vacuum regulator and reservoir. Both systolic and diastolic pressures are supplied to the 3 way diverter valve which drives a diaphragm pump.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A system for maintaining biological material comprising:
a chamber with a first check valve within the chamber controlling flow through the chamber, the chamber having an inlet and an outlet, the first check valve resisting back flow through the chamber from the outlet to the inlet;

biological material within the chamber;

a second check valve;

a conduit connecting the outlet of the chamber and the inlet of the chamber wherein the second check valve is located within the conduit such that the second check valve resists flow from the inlet of the chamber through the conduit;

a pump that provides pressure pulses connected to the chamber wherein a pressure pulse from the pump opens the first check valve, propels liquid through the outlet of the chamber and closes the second check valve, and wherein release of a pressure pulse closes the first check valve and opens the second check valve such that liquid flows through the second check valve into the chamber inlet, and a nutrient source comprising a source of nutrient solution and a second pump, the nutrient source being in fluid communication with the chamber.

2. The system of claim 1 further comprising a support disposed within the chamber for positioning the biological material.

3. The system of claim 1 wherein the biological material comprises a vascular graft or a heart valve graft, the biological material comprising biological tissue.

4. The system of claim 14 wherein the biological material comprises the first check valve.

5. The system of claim 3 wherein the biological material comprises a heart valve.

6. The system of claim 3 wherein the biological material comprises a vascular graft.

7. The system of claim 1 wherein the conduit is connected to an environmental control circuit comprising a heat exchanger.

8. The system of claim 1 wherein the chamber is a sterile, aseptic chamber.

9. The system of claim 1 wherein the pump is a diaphragm pump.

10. The system of claim 1 wherein the pump simulates conditions found in the human heart.

11. A method of maintaining biological material within a chamber having an inlet, an outlet and a first check valve that resists back flow from the outlet to the inlet, the method comprising circulating liquid through the chamber using a pulsed pump, wherein liquid flows through the chamber through the outlet when the pump applies pressure, and wherein a second check valve is located in a conduit from the inlet to the outlet such that the second check valve closes when the pump applies pressure and the second check valve opens when the pump releases pressure to provide for flow through the second check valve into the inlet and wherein a nutrient source is in fluid communication with the chamber, the nutrient source comprising a source of nutrient solution and a second pump.

12. The method of claim 11 wherein the biological material comprises biological tissue which functions as the first check valve.

13. The method of claim 11 wherein the pump is a diaphragm pump.

14. The method of claim 11 wherein competency of the biological material is tested.

15. The method of claim 11 wherein the biological material is seeded.

16. The method of claim 11 wherein the biological material is provided with nutrients and environmental control.

17. A system for maintaining biological material comprising:

a chamber with a first check valve within the chamber controlling flow through the chamber, the chamber having an inlet and an outlet, the first check valve resisting back flow through the chamber from the outlet to the inlet;

biological material within the chamber;

a second check valve;

a conduit connecting the outlet of the chamber and the inlet of the chamber wherein the second check valve is located within the conduit such that the second check valve resists flow from the inlet of the chamber through the conduit and wherein the first check valve and second check valve are not in a linear configuration;

a pump that provides pressure pulses connected to the chamber wherein a pressure pulse from the pump opens the first check valve, propels liquid through the outlet of the chamber and closes the second check valve, and wherein release of a pressure pulse closes the first check valve and opens the second check valve such that liquid flows through the second check valve into the chamber inlet; and viable cells not native to the biological material within the chamber.

18. The system of claim 17 further comprising a nutrient supply circuit in fluid communication with the chamber.

19. The system of claim 18 wherein the nutrient supply circuit comprises viable cells in a nutrient solution.

20. The system of claim 17 wherein the biological material comprises a heart valve and wherein the heart valve comprises the first check valve.

* * * * *